United States Patent
Shimada

(10) Patent No.: US 11,813,375 B2
(45) Date of Patent: Nov. 14, 2023

(54) THERAPEUTIC AGENT FOR SOLID CANCER

(71) Applicant: YANCHERS INC., Kyoto (JP)

(72) Inventor: Junichi Shimada, Kyoto (JP)

(73) Assignee: YANCHERS INC., Kyoto (JP)

( * ) Notice: Subject to any disclaimer, the term of this patent is extended or adjusted under 35 U.S.C. 154(b) by 274 days.

(21) Appl. No.: 16/315,756

(22) PCT Filed: Jul. 7, 2017

(86) PCT No.: PCT/JP2017/025044
§ 371 (c)(1),
(2) Date: Jan. 7, 2019

(87) PCT Pub. No.: WO2018/008761
PCT Pub. Date: Jan. 11, 2018

(65) Prior Publication Data
US 2019/0314545 A1    Oct. 17, 2019

(30) Foreign Application Priority Data
Jul. 8, 2016   (JP) .............................. 2016-153227

(51) Int. Cl.
*A61K 9/00*   (2006.01)
*A61L 24/06*   (2006.01)
(Continued)

(52) U.S. Cl.
CPC ............ *A61L 24/06* (2013.01); *A61K 31/695* (2013.01); *A61K 31/785* (2013.01); *A61K 49/0438* (2013.01); *A61L 2400/06* (2013.01)

(58) Field of Classification Search
CPC ..................................... A61L 24/05
See application file for complete search history.

(56) References Cited

U.S. PATENT DOCUMENTS

| | | | |
|---|---|---|---|
| 5,608,095 A | 3/1997 | Parker et al. | |
| 6,562,317 B2 | 6/2003 | Greff et al. | |

(Continued)

FOREIGN PATENT DOCUMENTS

| | | |
|---|---|---|
| EP | 0850065 B1 | 9/1999 |
| EP | 0900225 B1 | 1/2002 |

(Continued)

OTHER PUBLICATIONS

Fujita et al.: "Biological Activity of Organo Silicon Compounds—Study on Cancer Chemotherapeutic Activity", The Chemical Society of Japan, 1990, pp. 566-574, with Abstract.

(Continued)

*Primary Examiner* — Paul W Dickinson
(74) *Attorney, Agent, or Firm* — Birch, Stewart, Kolasch & Birch, LLP

(57) ABSTRACT

A novel therapeutic agent for solid cancer capable of hardening the cellular tissue itself of a solid cancer to induce death or growth inhibition of cancer cells, causing solidification of the tissue, is disclosed. The therapeutic agent for solid cancer is composed of a liquid composition containing as an active component an ethoxy-containing compound capable of undergoing polycondensation in a cellular tissue. The therapeutic agent for solid cancer is capable of hardening the cellular tissue itself of a solid cancer such as lung cancer to induce death or growth inhibition of cancer cells, causing solidification of the tissue. In conventional therapeutic methods, the risk of metastasis due to spreading of cancer cells through the bloodstream cannot be eliminated. In contrast, this therapeutic agent for solid cancer instantly surrounds cancer cells, so that the risk of metastasis can be largely reduced.

10 Claims, 1 Drawing Sheet

(51) Int. Cl.
    *A61K 31/695*     (2006.01)
    *A61K 31/785*     (2006.01)
    *A61K 49/04*     (2006.01)

(56) References Cited

U.S. PATENT DOCUMENTS

| | | | |
|---|---|---|---|
| 2006/0293280 A1 | 12/2006 | Uenishi et al. | |
| 2009/0004118 A1* | 1/2009 | Nie | A61K 49/0002 424/9.35 |
| 2013/0317418 A1 | 11/2013 | Freyman et al. | |
| 2016/0287717 A1* | 10/2016 | Brinker | A61K 9/5115 |
| 2017/0368206 A1* | 12/2017 | Alqathami | A61K 49/1818 |
| 2018/0214551 A1* | 8/2018 | Townley | A61L 24/001 |

FOREIGN PATENT DOCUMENTS

| | | |
|---|---|---|
| EP | 1506976 A1 | 2/2005 |
| EP | 2495243 A1 | 9/2012 |
| JP | 11-512404 A | 10/1999 |
| JP | 2001-509782 A | 7/2001 |
| JP | 2007-502306 A | 2/2007 |
| WO | WO 2011/052554 A1 | 5/2011 |

OTHER PUBLICATIONS

Hayashi et al., "Clinical Evaluation of Prophylactic Sclerotherapy for Esophageal Varices in Patients with Unresectable Hepatocellular Carinoma", Department of Internal Medicine, Tokyo Metropolitan Komagome Hospital, 1995, pp. 47-55, with Abstract.

The Written Opinion of the International Searching Authority (Form PCT/USA/237) for International Application No. PCT/JP2017/025044, dated Aug. 29, 2017, with English translation.

Wang et al., "Charge-Reversal APTES-Modified Mesoporous Silica Nanoparticles with High Drug Loading and Release Controllability", Applied Materials and Interfaces, vol. 8, Jun. 17, 2016, pp. 17166-17175.

Yamaki et al., "Compression Sclerotherapy for Varicose Veins: From Liquid to Foam", The Journal of Japanese College of Angiology, vol. 49, available online Aug. 27, 2009, pp. 225-231, with Abstract.

Zablotskaya et al., "Silyl Modification of Biologically Active Compounds. 11. Synthesis, Physico-Chemical and Biological Evaluation of N-(Trialkoxysilylallkyl) Tetrahydro(Iso,Silaiso) Quinoline Derivatives", Applied Organometallic Chemistry, vol. 20., Avail. online Nov. 28, 2005, pp. 149-154.

* cited by examiner

THERAPEUTIC AGENT FOR SOLID CANCER

TECHNICAL FIELD

The present invention relates to a therapeutic agent for solid cancer.

BACKGROUND ART

Due to the recent progress in computer technologies, 16-row scanning has become common for CT scanners, and a three-dimensional study of a lung lesion by 320-row CT scanning has been reported in the meeting of The Japanese Association for Thoracic Surgery in autumn 2012. A further exponential improvement of the radiation diagnostic imaging performance can be expected in the future. Since "air" is a highly radiolucent matter, it is depicted in black. The organ "lung", containing a large amount of "air", basically has an extremely high S/N ratio in image representation, and therefore its small lesions can be easily visualized. Because of this, finding of small lung cancers with ground-glass appearances has become possible. When a remarkable improvement in the diagnostic performance is achieved in the future, one might be able to say, for example, "seven cells have been changed into lung cancer" in diagnosis based on the alveolar cell size. If diagnostic devices equipped with artificial intelligence are developed in the future, a further increase in the lesion detection rate can be expected, and the frequency of detection of lung cancer lesions with ground-glass appearances may increase worldwide at an accelerated rate, leading to a further increase in the number of patients.

In the alveolus, which is the basic structure of the lung, a chamber containing air is surrounded by thin and flat alveolar cells such that gas exchange between oxygen and carbon dioxide in the lung is possible. In the vicinity of the cells constituting the alveolus, water in the inner cavity of the alveolus, water in body fluids such as blood for supplying nutrients to cells, lipids in the cell walls of the alveolar cells themselves, water in the cytoplasm, and the like are present. In alveolar cell carcinoma, which is an early-stage lung cancer, such cells constituting the alveolus become cancer, and exhibit abnormal growth.

Surgical treatment of lung cancer is based on local treatment of the cancer using an action of physically removing the target. Although such treatment includes lobectomy, segmentectomy, and partial excision, and varies in terms of the range of removal and the anatomical technique, the treatment is basically local treatment. Radiation therapy is also based on local treatment using an action of cell injury by physical energy of radiation. Although radiation therapy varies in terms of the device used therefor, it is local treatment. Radiofrequency ablation is based on use of an action to ablate cancer cells by heat generated by radio waves, and this treatment, including the so-called thermotherapy, which is carried out by heating at about 43° C. and capable of performing treatment over a broader area, is local treatment. Tissue freezing treatment is a local treatment that attempts to kill a cellular tissue by removing heat to freeze the tissue.

Although innovations have been made in local treatment methods for cancers due to the progress of technologies as described above, any of these is intended for injury of a cancer cell tissue using a local physical action.

PRIOR ART DOCUMENTS

Non-Patent Documents

[Non-patent Document 1] 1) Clinical evaluation of prophylactic sclerotherapy for esophageal varices in patients with unresectable hepatocellular carcinoma. Journal of Japanese Society of Gastroenterology 92(1) 47-55, 1995
[Non-patent Document 2] 2) Compression sclerotherapy for varicose veins: from liquid to foam. The Journal of Japanese College of Angiology Vol. 49, 2009

SUMMARY OF THE INVENTION

Problems to be Solved by the Invention

Improvement of diagnostic accuracy and an increase in patients with malignant neoplasm due to the aging society have led to a rapidly increasing number of small lesions of lung cancer. Elderly patients are less tolerant of operations, and typical operations are not safely acceptable to them in some cases. In cases of small and multiple lesions, their complete removal by surgery is impossible. In cases of simultaneous occurrence of diseases such as development of a plurality of types of cancers at the same time, their complete curative treatment is impossible. In radiation therapy, there is an upper limit of the total therapeutic radiation dose.

Under the above-described circumstances, an object of the present invention is to provide a novel therapeutic agent for solid cancer capable of hardening the cellular tissue itself of a solid cancer to induce death or growth inhibition of cancer cells, causing solidification of the tissue.

Means for Solving the Problems

As a result of intensive study, the present inventors discovered that a liquid composition containing an ethoxy-containing compound can infiltrate into a solid cancer cellular tissue, and then be hardened by a reaction in which water in the body is involved, and that death or growth inhibition of the solid cancer cells can be induced by the resulting hardened matter, as well as ethanol released during the hardening reaction and heat generated by exothermic reaction, thereby completing the present invention.

That is, the present invention provides the following.
(1) A therapeutic agent for solid cancer composed of a liquid composition containing as an active component an ethoxy-containing compound capable of undergoing polycondensation in a cellular tissue.
(2) The therapeutic agent for solid cancer according to (1), wherein the ethoxy-containing compound is an ethoxy-containing silicon compound.
(3) The therapeutic agent for solid cancer according to (2), wherein the ethoxy-containing silicon compound is an ethoxysilane compound.
(4) The therapeutic agent for solid cancer according to (3), wherein the ethoxysilane compound is at least one selected from the group consisting of ethyl silicate and condensates thereof, and methyltriethoxysilane and condensates thereof.
(5) The therapeutic agent for solid cancer according to any one of (1) to (4), further comprising a cyanoacrylate-based monomer.
(6) The therapeutic agent for solid cancer according to (5), wherein the cyanoacrylate-based monomer is at least one selected from the group consisting of methyl 2-cyanoacrylate, ethyl 2-cyanoacrylate, iso-propyl 2-cyanoacrylate, n-propyl 2-cyanoacrylate, n-butyl 2-cyanoacrylate, iso-butyl 2-cyanoacrylate, t-butyl 2-cyanoacrylate, hexyl 2-cyanoacrylate, ethoxyethyl 2-cyanoacrylate, octyl 2-cyanoacrylate, and bis(alkylene 2-cyanoacrylate) compounds.

(7) The therapeutic agent for solid cancer according to any one of (1) to (6), further comprising a transition metal ethoxide.

(8) The therapeutic agent for solid cancer according to (7), wherein the transition metal ethoxide is titanium ethoxide.

(9) The therapeutic agent for solid cancer according to any one of (1) to (8), further comprising an X-ray contrast agent or an MRI contrast agent.

(10) The therapeutic agent for solid cancer according to any one of (1) to (9), wherein the solid cancer is lung cancer.

(11) The liquid composition recited in any one of (1) to (10), for use in the treatment of solid cancer.

(12) A method of treating a solid cancer, comprising administering the liquid composition recited in any one of (1) to (10) to a cancer tissue of a solid cancer patient.

Effects of the Invention

The present invention provided a novel therapeutic agent for solid cancer capable of causing site-specific death or growth inhibition of solid cancer cells. Since the therapeutic agent for solid cancer of the present invention is a liquid, and can be directly administered to a cancer tissue by injection using a thin injection needle, it is less invasive, and does not require tissue ablation. Therefore, the burden on the patient is small, and it is readily applicable to elder patients. The agent is readily applicable even in cases where a plurality of cancer tissues have developed in one organ.

MODE FOR CARRYING OUT THE INVENTION

Figure 1:
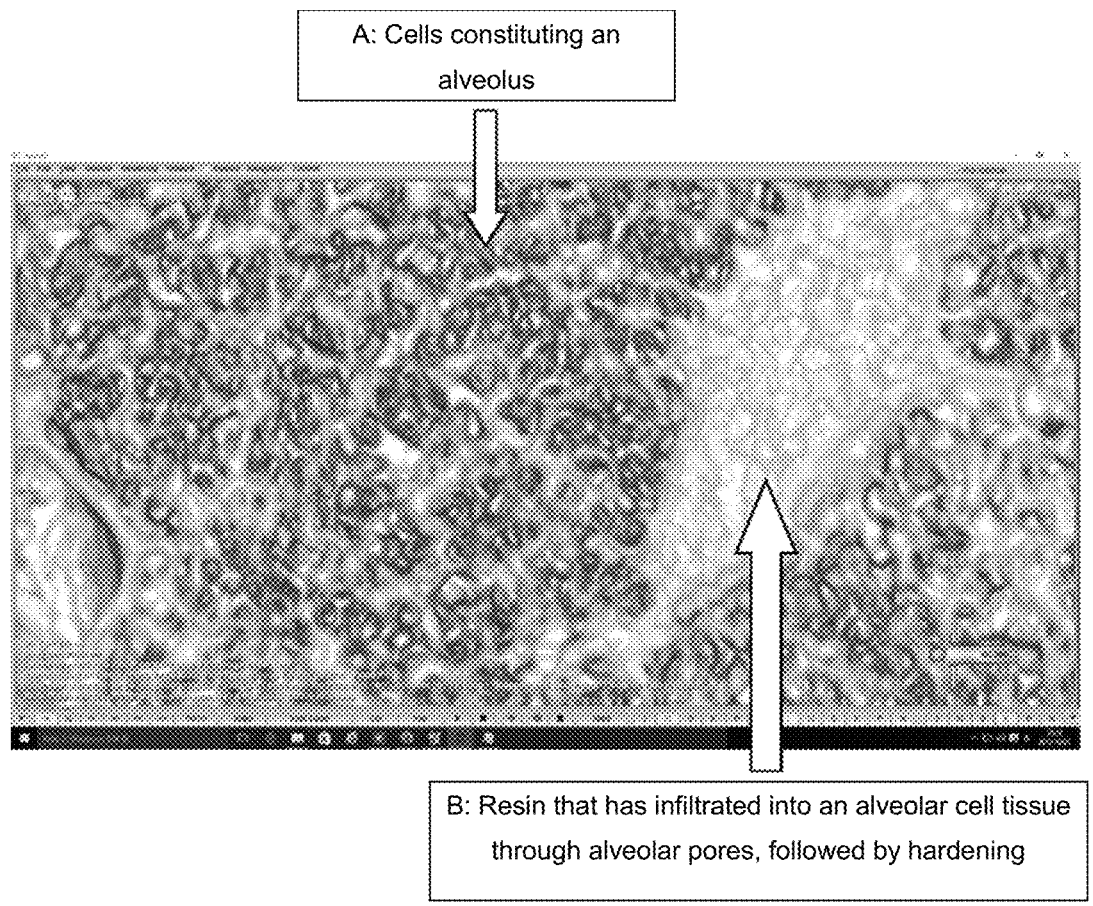
FIG. 1 is a laboratory micro-CT photograph obtained by injection of the therapeutic agent for solid cancer of the present invention into a rat lung. In the structure (A) of cells constituting an alveolus, hardened composition (B) can be found.

As described above, the therapeutic agent for solid cancer of the present invention is composed of a liquid composition containing as an active component an ethoxy-containing compound capable of undergoing polycondensation in a cellular tissue. The "cellular tissue" means a body tissue containing cells. Since a cellular tissue contains water, the composition infiltrates into the cellular tissue, and is then hardened by a reaction in which water in the body is involved. Further, when polycondensation occurs in the cellular tissue, ethanol is produced by hydrolysis of ethoxy groups, and the ethanol plays a useful role in causing death or growth inhibition of cancer cells.

Examples of the ethoxy-containing compound include various metal ethoxide compounds. Taking injection into the body into account, use of compounds with harmful metal ions should be avoided. In view of this, examples of the metal include silicon, titanium, zirconium, aluminum, and bismuth. Among these, silicon and titanium are preferably used. Ethoxy-containing silicon compounds are especially preferred. Among these metal ethoxides, transition metal ethoxides can increase the hardening rate in the body, so that they can be used as additives. This will be described later.

Examples of the ethoxy-containing silicon compounds include a large number of silicon compounds containing an ethoxy group. Examples of such compounds that can be hardened and can have three-dimensional structures include trifunctional silane compounds and tetrafunctional silane compounds.

As organic functional groups of the trifunctional silane compounds, a $C_1$-$C_{10}$ substituent, preferably an alkyl group, can be employed. Among alkyl groups, from the viewpoint of reduction of adverse effects on the body, and easy formation of a three-dimensional cross-linked structure, methyl group is preferably used as the substituent.

Specific examples of the compounds include methyltriethoxysilane compounds. In order to prevent volatilization and dispersion after injection into the body, these are preferably used in the form of oligomer structures prepared by preliminarily allowing dehydration condensation.

The oligomerization can be carried out by adding an appropriate amount of water to a trifunctional silane compound such as methyltriethoxysilane, and sequentially allowing partial hydrolysis and dehydration condensation. Although the partial hydrolysis can be carried out at room temperature, it may also be carried out under heat for increasing the reaction rate. The amount of water used for the partial hydrolysis is not limited, and usually 0.5 to 2 moles, preferably about 0.8 to 1.2 moles per 1 mole of the silane compound. The length of time of the partial hydrolysis reaction is not limited. It is preferred to keep stirring until the hydrolysis reaction mixture becomes transparent. The length of time is usually about one day and night (not less than 12 hours). Oligomerization due to condensation proceeds at the same time as the partial hydrolysis, to produce oligomers such as dimer, trimer, and tetramer. Alcohols such as ethanol produced during the partial hydrolysis are preferably removed from the viewpoint of local inhibition of the cell growth upon injection into a tissue. The removal of alcohol can be carried out under heat using an evaporator or the like. The evaporator is used under a reduced pressure of about 60 mmHg at a temperature of usually 30° C. to 70° C. for about 10 minutes to 60 minutes. For allowing the hydrolysis reaction to proceed rapidly, an acidic water may be added.

Examples of the tetrafunctional silane compounds include tetraethyl silicate. Similarly to the trifunctional silane compounds such as methyltriethoxysilane, these compounds are also preferably used in the faun of an oligomer structure prepared by preliminarily allowing dehydration condensation as described above in order to prevent volatilization and dispersion after injection into the body.

The oligomerization of these compounds can be carried out in the same manner as in the cases of trifunctional silane compounds. By selecting conditions, oligomer compounds having structures with various degrees of condensation such as dimer, trimer, and tetramer can be formed.

The trifunctional silane compounds and the tetrafunctional silane compounds may be used individually, or two or more of these may be used in combination. For the purpose of controlling the hardening rate, a trifunctional silane compound(s) and a tetrafunctional silane compound(s) may be used as a mixture.

The composition used in the present invention preferably further contains a cyanoacrylate-based monomer. Since a cyanoacrylate-based monomer functions as an organic component that controls the reaction rate, and generates heat to about 50° C. during polymerization, death or growth inhibition of cancer cells can be induced by this heat. Cyanoacrylate compounds are used for closure of the skin during operations, and skin approximation during operations. They react with moisture on the skin surface to cause a temperature rise to about 50° C., and then undergo resinification. They can be said to be preferred components because of the exothermic reaction.

A number of compounds have been developed as cyanoacrylates, and they are commercially available. Specific examples of monofunctional cyanoacrylate compounds include methyl 2-cyanoacrylate, ethyl 2-cyanoacrylate, isopropyl 2-cyanoacrylate, n-propyl 2-cyanoacrylate, n-butyl 2-cyanoacrylate, iso-butyl 2-cyanoacrylate, t-butyl 2-cyanoacrylate, hexyl 2-cyanoacrylate, ethoxyethyl 2-cyanoacrylate, and octyl 2-cyanoacrylate.

Further, by using a bis(alkylene 2-cyanoacrylate) compound as a bifunctional compound, a three-dimensional cross-linked structure can be formed by itself. Specific examples of the bis(alkylene 2-cyanoacrylate) compound include bis(methylene 2-cyanoacrylate) and bis(butylene 2-cyanoacrylate). When such a cyanoacrylate compound capable of forming a three-dimensional cross-linked structure by itself is used, the cyanoacrylate compound itself can be used as a therapeutic agent for solid cancer even without use of the ethoxy-containing compound.

These cyanoacrylate compounds may be used not only individually, but also as a mixture of two or more thereof. Further, for adjusting viscosity of the cyanoacrylate compounds, those supplemented with a thickener are also preferably used.

Examples of the thickener that may be used include acrylic compounds such as polymethyl methacrylate, cellulosic compounds, and silicone compounds such as polydimethylsiloxane. The amount of the thickener added is not limited as long as the later-mentioned preferred viscosity can be achieved therewith, and normally not more than 30% by weight.

The viscosity of the cyanoacrylate compound may be appropriately selected based on, for example, the type and the composition ratio of the ethoxy-containing compound used in combination.

For rapid hardening of the composition used in the present invention after its injection into a cellular tissue, and for enabling release of ethanol, the composition may contain an ethoxylated transition metal compound as the ethoxide compound. By the inclusion of the ethoxylated transition metal compound, the hardening reaction can be allowed to proceed more rapidly. This enables more localized injection of the composition to a cancer tissue.

Such an ethoxylated transition metal compound is to be selected based not only on its ability to control the reactivity, but also on the fact that use of a harmful metal ion should be avoided taking its injection into the body into account. In view of this, titanium compounds are preferred.

Examples of the titanium compounds capable of controlling the reactivity include titanium ethoxide compounds, which react with water in the body and is capable of releasing ethanol. The titanium ethoxide compound is preferably a tetrafunctional titanium tetraethoxide.

Similarly to the ethoxy-containing silicon compounds described above, the titanium ethoxide compound is preferably preliminarily subjected to partial condensation to allow oligomerization before use.

The composition used in the present invention is a liquid, and used in a solvent-free system. In cases where the ethoxy-containing compound is used after oligomerization, the water produced by this process may be used as it is as the hydrolysis water.

The composition ratio of each component in the composition of the present invention may be appropriately selected based on, for example, the site to which the composition is to be injected. Normally, the ethoxy-containing silicon compound and/or a condensate thereof is preferably in an amount of 1 part by weight to 1000 parts by weight, and the titanium compound and/or a condensate thereof is preferably in an amount of 0.01 part by weight to 10 parts by weight, with respect to 100 parts by weight of the cyanoacrylate compound. The concentration of the ethoxy-containing silicon compound in the composition is usually about 5% by weight to 90% by weight with respect to the total weight of the composition.

The viscosity of the composition is preferably adjusted to a viscosity that enables injection through a 22-gauge needle, which causes less pain upon puncture. More specifically, the liquid viscosity at the time of injection is from 1 mPaS to 100 mPaS. For enabling injection without application of an excessive force, the liquid viscosity is preferably not more than 60 mPaS, more preferably not more than 40 mPaS. From the viewpoint of easy injection and prevention of liquid leakage, the liquid viscosity is most preferably from 2 mPaS to 30 mPas. The concentration of each component can be selected such that the composition has such a viscosity. In addition, the thickener described above may be added, if necessary.

Since the composition used in the present invention contains silicon atoms and/or titanium atoms, the composition can be visualized by X-ray CT, MRI, or the like. For obtaining a clearer image, an X-ray contrast agent or an MRI contrast agent may be added thereto. The amount of the contrast agent added is appropriately selected, and usually about 0.1% by weight to 5% by weight.

The solid cancer to be treated with the therapeutic agent of the present invention is not limited, and preferably lung cancer, renal cancer, gastric cancer or the like. Lung cancer is especially preferred.

When a solid cancer is treated by application of the therapeutic agent for solid cancer of the present invention, an injection needle is moved toward the cancer tissue (for example, toward a portion with a ground-glass appearance in lung cancer) while performing CT imaging by high-resolution CT, and then the composition liquid is injected. In the future, due to improvement of the performance of the magnetic body and improvement of the performance of the magnetic sensor, and for avoiding radiation exposure to medical staffs, injection-hardening therapy under MRI imaging on an outpatient basis may become possible. The insertion of the injection needle may also be preferably carried out under ultrasound imaging.

Injection of the liquid composition used in the present invention into a cellular tissue causes hydrolysis of ethoxy groups by water in the body to produce ethanol, and, at the same time, condensation of oligomers occur to cause their resinification and hardening. Death or growth inhibition of cancer cells is induced by the hardening, an action of the ethanol, and the hyperthermic effect due to the heat produced during the hardening.

The therapeutic agent for solid cancer of the present invention or a preferred mode thereof has the following excellent properties, and is effective for treatment of a solid cancer in a very early stage.

(1) The agent is a liquid composition that infiltrates into a cellular tissue followed by hardening of the composition by a reaction in which water in the body is involved.
(2) The agent has a cell-growth inhibitory effect produced by infiltration into a cellular tissue and subsequent hardening due to exothermic reaction caused by water in the body.
(3) Since hardening reaction of the composition is promoted not only by water in the cellular tissue in the body, but also by involvement of lecithin, effective prevention of leakage of the composition from the cellular tissue can be expected.
(4) Since the composition contains an ethoxy compound, it has a property to release ethanol, and has a significant cell-growth inhibitory effect.
(5) Since the ethoxysilane compound contained is less likely to undergo decomposition in the body, the cell-growth inhibitory effect is maintained for a long period.
(6) Since a titanium catalyst is contained, the agent has a property to release ethanol, and moreover, the hardening rate can be controlled, so that treatment can be easily performed by a physician.
(7) Because of addition of an organic component for control of the reaction rate, leakage of the agent to the outside of the cells in the affected area can be prevented.
(8) Since the organic component for control of the reaction rate is a cyanoacrylate-based monomer, the reaction caused by water in the body is an exothermic reaction. Therefore, by infiltration into the cellular tissue and subsequent hardening, the agent can produce a significant cell-growth inhibitory effect.
(9) The agent infiltrates into voids and the like in a tissue, and reacts with water in the cellular tissue in the body. The reaction is accelerated by the body heat to cause chemical hardening of the agent, leading to physical blocking of the cellular tissue.
(10) Since the agent is in a liquid form having a viscosity which allows its injection into the site of interest through a biopsy needle or an endoscopic catheter, treatment can be easily performed.
(11) The agent can be visualized by imaging with an image analyzer such as a fluoroscope or an X-ray tomograph, to allow observation by the imaging.
(12) The agent can be visualized by imaging with an image analyzer such as an MRI apparatus, to allow observation by the imaging.
(13) The agent can be provided with functions such as initiation of polymerization by water present in the body, release of heat of polymerization, favorable biocompatibility, and cancer cell-killing function by the release of ethanol upon polymerization. Regarding the biocompatibility, since contact lenses and silicone rubber products have been widely used as medical devices, the agent can be a material applicable to the human body even without changing its physical properties.
(14) Since the position of the resin after hardening can be accurately identified by a diagnostic imaging device, an additional composition can be administered by infusion, if necessary.

The present invention is described below more concretely by way of Examples. However, the present invention is not limited to the following Examples.

EXAMPLES

Example 1

Trimethylsiloxysilicate (trade name, MQ-1600; manufactured by Dow Corning Toray Co., Ltd.), 3-aminopropyltriethoxysilane (trade name, Z-6011; manufactured by Dow Corning Toray Co., Ltd.), and hydroxyl-terminated polydimethylsiloxane (trade name, PMX-0156; manufactured by Dow Corning Toray Co., Ltd.) were mixed together at a weight ratio of 5:3:2, and the resulting mixture was mixed with Iomeprol (nonionic X-ray contrast agent). As a result of observation of the state of hardening of the mixture at room temperature, a capacity to pass through a syringe for injection into a tissue and occurrence of gelation in several minutes could be confirmed. Regarding visualization by X-ray CT, the mixture was found to be clearly visible when Iomeprol was mixed at about 5 wt %.

Example 2

Preparation of Ethoxylated Compound-Containing Composition

To 1 mole of methyltriethoxysilane, about an equimolar amount of water was added, and the resulting mixture was stirred until the mixture became transparent, to prepare a hydrolysate. Thereafter, ethanol produced in the hydrolysate was removed using an evaporator under heat and reduced pressure (50° C., 30 minutes), to obtain an oligomer compound of methyltriethoxysilane (1).

(2) Preparation of Liquid Composition

Preparation of Liquid A: By mixing 2.42 parts of the oligomer compound (1) prepared in the above section (1) with 0.08 part of titanium tetraethoxide, Liquid A was prepared.

Liquid B: A commercially available product of iso-butyl 2-cyanoacrylate was used.

Preparation of Composition: Immediately before use, 0.25 part of Liquid A and 0.75 part of Liquid B were mixed together to provide a liquid composition.

(3) Injection Test Using Rats

With a 29-G injection needle, 0.03 mL of the liquid composition prepared in (2) was injected into a rat lung. Hardening and immobilization of the injected resin, and the absence of its leakage to the outside of the injection site, were confirmed with a CT imaging device and an MRI imaging device. A photograph taken by laboratory micro-CT during this operation is shown in FIG. 1. As shown in FIG. 1, in the structure of cells (A) constituting an alveolus, the injected composition (B) can be found.

Example 3

The same experiment as in Example 2 was carried out except that Liquid B was iso-butyl 2-cyanoacrylate/ethyl 2-cyanoacrylate=2/1 (weight ratio). The same result was obtained in the injection test using rats.

Example 4

The same experiment as in Example 2 was carried out except that Liquid A was 2.48 parts of the oligomer compound (1) and 0.02 part of titanium tetraethoxide, and that Liquid B was i-butyl 2-cyanoacrylate/iso-propyl 2-cyanoacrylate=2/1 (weight ratio). The same result was obtained in the injection test using rats.

Example 5

Preparation of Liquid A: By mixing, as an ethoxylated silicone resin, 2.4 parts of the oligomer compound (1) obtained from the methyltriethoxysilane prepared in Example 1 with 2.4 parts of a commercially available product of ethyl silicate oligomer compound and 0.1 part of titanium tetraethoxide, Liquid A was prepared.

Liquid B: A commercially available product of ethyl 2-cyanoacrylate supplemented with a PMMA-based thickener was used.

Preparation of Liquid Composition: Immediately before use, 0.25 part of Liquid A and 0.75 part of Liquid B were mixed together to provide a liquid composition.

The obtained composition was stable at room temperature for 2 hours, and had stability that enables its injection into an affected area through an injection needle. Furthermore, the composition had properties that cause infiltration of the composition into a cellular tissue followed by hardening by a reaction in which water in the body is involved.

Example 6

For the purpose of evaluating hardening properties of the obtained composition in vitro, 0.075 part by weight of lecithin was added to 1 part by weight of the composition described in Example 5. As a result, immediate gelation of the composition was found, and it could therefore be confirmed that the hardening reaction proceeds at a very high reaction rate.

Figure 2:
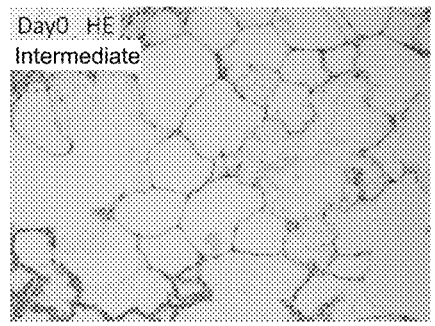
FIG. 2 is a micrograph of a sample obtained by hematoxylin-eosin (HE) staining of a lung tissue after injection of the therapeutic agent for solid cancer of the present invention to a rat lung (magnification, ×400).

Further, in the same manner as described above, a rat lung tissue obtained after injection of the therapeutic agent for solid cancer of the present invention to the lung was removed, and subjected to hematoxylin-eosin (HE) staining. The results are shown in FIG. 2 (magnification, ×400). Resinification of the composition, and necrosis of alveolar epithelial cells in the vicinity of the resin can be found.

INDUSTRIAL APPLICABILITY

The therapeutic agent for solid cancer of the present invention is capable of hardening the cellular tissue itself of a solid cancer to induce death or growth inhibition of cancer cells, causing solidification of the tissue. The agent is therefore useful as a therapeutic agent for solid cancer in the field of medicine. In conventional therapeutic methods, the risk of metastasis due to spreading of cancer cells through the bloodstream cannot be eliminated. In contrast, the therapeutic agent for solid cancer of the present invention instantly surrounds cancer cells, so that the risk of metastasis can be largely reduced.

The invention claimed is:

1. A method of killing solid cancer cells or inhibiting growth of solid cancer cells, which comprises injecting an effective amount of a liquid composition containing as an active component an ethoxy-containing compound, which undergoes a polycondensation reaction in a cellular tissue after injection, into a solid cancer, wherein the liquid composition is injected in an amount effective to kill solid cancer cells or inhibit growth of solid cancer cells in said tissue in said patient, and wherein said liquid composition further contains a transition metal ethoxide.

2. The method of claim 1, wherein said ethoxy-containing compound is an ethoxy-containing silicon compound.

3. The method of claim 2, wherein said ethoxy-containing silicon compound is an ethoxysilane compound.

4. The method of claim 3, wherein said ethoxysilane compound is at least one selected from the group consisting of ethyl silicate and condensates thereof, and methyltriethoxysilane and condensates thereof.

5. The method of claim 1, wherein said therapeutic agent further comprises a cyanoacrylate-based monomer.

6. The method of claim 5, wherein said cyanoacrylate-based monomer is at least one selected from the group consisting of methyl 2-cyanoacrylate, ethyl 2-cyanoacrylate, iso-propyl 2-cyanoacrylate, n-propyl 2-cyanoacrylate, n-butyl 2-cyanoacrylate, iso-butyl 2-cyanoacrylate, t-butyl 2-cyanoacrylate, hexyl 2-cyanoacrylate, ethoxyethyl 2-cyanoacrylate, octyl 2-cyanoacrylate, and bis(alkylene 2-cyanoacrylate) compounds.

7. The method of claim 2, wherein said transition metal ethoxide is titanium ethoxide.

8. The method of claim 1, wherein said therapeutic agent further comprises an X-ray contrast agent or an MRI contrast agent.

9. The method of claim 1, wherein said solid cancer is lung cancer.

10. The method of claim 5, wherein said liquid composition is prepared by mixing, immediately before injection, a liquid A comprising said ethoxy-containing compound and said transition metal ethoxide and a liquid B comprising said cyanoacrylate-based monomer.

* * * * *